(12) United States Patent
Marquis, Jr. et al.

(10) Patent No.: US 6,534,498 B1
(45) Date of Patent: Mar. 18, 2003

(54) PROTEASE INHIBITORS

(75) Inventors: Robert W. Marquis, Jr., Wayne, PA (US); Yu Ru, Wayne, PA (US); Daniel Frank Veber, Ambler, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 10/129,681

(22) PCT Filed: Nov. 8, 2000

(86) PCT No.: PCT/US00/30684

§ 371 (c)(1),
(2), (4) Date: May 6, 2002

(87) PCT Pub. No.: WO01/34156

PCT Pub. Date: May 17, 2001

(30) Foreign Application Priority Data

Nov. 10, 1999 (US) .......................................... 60164578

(51) Int. Cl.[7] ...................... A61K 31/55; C07D 401/14; A61P 19/09; A61P 19/10
(52) U.S. Cl. ................... 514/217.07; 540/597
(58) Field of Search ....................... 514/212.08, 217.07; 540/597

(56) References Cited

U.S. PATENT DOCUMENTS

| | | | |
|---|---|---|---|
| 4,038,247 A | 7/1977 | Muller et al. | 260/45.9 |
| 4,447,419 A | 5/1984 | Quadro | 424/177 |
| 4,518,528 A | 5/1985 | Rasnick | 260/112.5 R |
| 4,638,010 A | 1/1987 | Weller, III et al. | 514/423 |
| 4,749,792 A | 6/1988 | Natarajan et al. | 546/312 |
| 4,994,471 A | 2/1991 | Lalinde et al. | 514/326 |
| 5,057,525 A | 10/1991 | Van Daele | 514/318 |
| 5,142,056 A | 8/1992 | Kempe et al. | 546/265 |
| 5,206,251 A | 4/1993 | Khanna et al. | 514/315 |
| 5,216,168 A | 6/1993 | Khanna et al. | 546/242 |
| 5,374,637 A | 12/1994 | Van Daele | 514/320 |
| 5,395,824 A | 3/1995 | Higuchi et al. | 514/19 |
| 5,422,359 A | 6/1995 | Ando et al. | 514/365 |
| 5,424,325 A | 6/1995 | Ando et al. | 514/357 |
| 5,501,969 A | 3/1996 | Hastings et al. | 435/240.2 |
| 5,523,313 A | 6/1996 | Nunami et al. | 514/365 |
| 5,585,387 A | 12/1996 | Lu et al. | 514/327 |
| 5,668,128 A | 9/1997 | Tsubotani et al. | 514/183 |
| 5,830,850 A | 11/1998 | Gelb et al. | 514/2 |
| 5,861,298 A | 1/1999 | DeBouck et al. | |
| 5,902,882 A | 5/1999 | Matzinger et al. | 540/604 |
| 5,948,669 A | 9/1999 | Field et al. | |
| 5,998,470 A | 12/1999 | Halbert et al. | 514/482 |
| 6,057,362 A | 5/2000 | Yamashita | 514/468 |
| 6,232,342 B1 | 5/2001 | Carr et al. | 514/524 |
| 6,274,336 B1 | 8/2001 | Abdel-Meguid et al. | |
| 6,284,777 B1 | 9/2001 | Halbert et al. | 514/332 |
| 6,331,542 B1 | 12/2001 | Carr et al. | 514/237.8 |

FOREIGN PATENT DOCUMENTS

| | | |
|---|---|---|
| EP | 0 237 082 A | 9/1987 |
| EP | 0 504 938 A2 | 3/1992 |
| EP | 0 525 420 A1 | 2/1993 |
| EP | 0 543 310 | 5/1993 |
| EP | 0 603 873 A1 | 6/1994 |
| EP | 0 611 756 A2 | 8/1994 |
| EP | 0 623 592 | 11/1994 |
| WO | WO 92/04371 | 3/1992 |
| WO | WO 94/00095 | 1/1994 |
| WO | WO 94/04172 | 3/1994 |
| WO | WO 94/23033 | 10/1994 |
| WO | WO 95/05192 | 2/1995 |
| WO | WO 95/24182 A | 9/1995 |
| WO | WO 96/13523 | 5/1996 |
| WO | WO 96/40737 | 12/1996 |
| WO | WO 97/16433 | 5/1997 |
| WO | WO 97/47642 | 12/1997 |
| WO | WO 97/47643 | 12/1997 |
| WO | WO 97/49668 | 12/1997 |
| WO | WO 98/05336 | 2/1998 |
| WO | WO 98/08802 | 3/1998 |
| WO | WO 98/12211 | 3/1998 |
| WO | WO 98/48799 | 11/1998 |
| WO | WO 98/49152 | 11/1998 |
| WO | WO 98/50342 | 11/1998 |
| WO | WO 99/11637 | 3/1999 |
| WO | WO 99/53039 | 10/1999 |
| WO | WO 99/59526 | 11/1999 |
| WO | WO 99/59570 | 11/1999 |
| WO | WO 99/64399 | 12/1999 |
| WO | WO 99/66925 | 12/1999 |
| WO | WO 00/29408 | 5/2000 |
| WO | WO 01/34160 | 5/2000 |
| WO | WO 00/38687 | 7/2000 |

(List continued on next page.)

OTHER PUBLICATIONS

Bossard, et al., (1996), J. of Bio. Chem;, vol. 271, No. 21, pp. 12517–12524.

(List continued on next page.)

*Primary Examiner*—Alton N Pryor
(74) *Attorney, Agent, or Firm*—Linda E. Hall; Stephen Venetianer; Charles M. Kinzig

(57) ABSTRACT

This invention relates to the compound of Formula (I) or a pharmaceutically acceptable salt, hydrate or solvate thereof, which is an inhibitor of cysteine proteases, particularly cathepsin K, and is useful in the treatment of diseases in which inhibition of bone loss or of cartilage degradation is a factor.

(I)

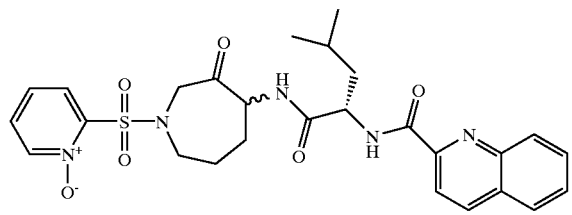

17 Claims, No Drawings

FOREIGN PATENT DOCUMENTS

| WO | WO 00/39115 | 7/2000 |
|---|---|---|
| WO | WO 00/49011 | 8/2000 |
| WO | WO 00/54769 | 9/2000 |
| WO | WO 00/58296 | 10/2000 |
| WO | WO 01/34153 | 5/2001 |
| WO | WO 01/34154 | 5/2001 |
| WO | WO 01/34155 | 5/2001 |
| WO | WO 01/34156 | 5/2001 |
| WO | WO 01/34157 | 5/2001 |
| WO | WO 01/34158 | 5/2001 |
| WO | WO 01/34159 | 5/2001 |
| WO | WO 01/34565 | 5/2001 |
| WO | WO 01/34566 | 5/2001 |
| WO | WO 01/34599 | 5/2001 |
| WO | WO 01/70232 | 9/2001 |
| WO | WO 02/17924 | 3/2002 |

OTHER PUBLICATIONS

Bromme, et al., (1996), Biochemical Journal, vol. 315, pp. 85–89, especially abstract, Figure 1.

Velasco, et al., (1994), J. of Bio. Chem; vol. 269, No. 43, pp. 27136–27142, especially the abstract.

Magrath, et al., (1992), J. of Med. Chem; vol. 35, No. 23, pp. 4279–4283, especially p. 4281, col. 1, structures 1–4 and 7.

Graybill, et al., (1992), Bioorganic & Medicinal Chemistry Letters; vol. 2, No. 11, pp. 1375–1380, especially p. 1377, Scheme I.

Palmer, et al., (1995), J. of Med. Chem; vol. 38, No. 17, pp. 3193–3196.

Danheiser, (1995), Genetic Engineering News; vol. 15, No. 17, pp. 1–1 and 35–36.

Rasnick, (1996), Perspectives in Drug Discovery & Design; vol. 6, pp. 47–63.

Potempa, et al., "Host and *Porphyromonas gingivalis* proteinases in periodontitis: A biochemical model of infection and tissue destruction", (1994), Perspectives in Drug Discovery and Design, vol. 2, pp. 445–458.

Drake, et al., "Cathepsin K, but Not Cathepsins B, L, or S, Is Abundantly Expressed in Human Osteoclasts", (1996), J. of Biological Chemistry, 271 (21), pp. 12511–12516.

Bromme, et al., "Human Cathepsin O2, a Matrix Protein–degrading Cysteine Protease Expressed in Osteoclasts", (1996), J. of Biological Chemistry, 271 (4), pp. 2126–2132.

Delaisse, et al., "In Vivo and In Vitro Evidence for the Involvement of Cysteine Proteinases in Bone Resorption", (1984), Biochemical and Biophysical Research Communications, 125 (2), pp. 441–447.

Delaisse, et al., "Inhibition of bone resorption in culture by inhibitors of thiol proteinases", (1980), Biochem. J., 192, pp. 365–368.

Lerner, et al., "Human Cystatin C, a Cysteine Proteinase Inhibitor, Inhibits Bone Resporption In Vitro Stimulated by Parathyroid Hormone and Parathyroid Hormone–Related Peptide of Malignancy", (1992), J. of Bone and Mineral Research, 7 (4), pp. 433–439.

Hill, et al., "Inhibition of Bone Resorption by Selective Inactivators of Cysteine Proteinases", (1994), J. of Cellular Biochemistry, 56, pp. 118–130.

Delaise, et al., "The Effects of Inhibitors of Cysteine–Proteinases and Collagenase on the Resorptive Activity of Isolated Osteoclasts", Bone, 8, pp. 305–313.

Borg, et al, "Synthesis of 1,2,4–Oxadiazole–, 1,3,4–Oxadiazole–, and 1,2,4–Triazole–Derived Dipeptidomietics", J. Org. Chem., 60, pp. 3112–3120.

Boden, et al, "Total Synthesis of Lissoclinamide 5, a Cytotoxic Cyclic Peptide from the Tunicate *Lissoclinum patella*", (1994), Tetrahedron. Ltrs., 35 (44), pp. 8271–8274.

U.S. patent application Ser. No. 09/078,314, Field et al., filed May 13, 1998.

Everts, et al., "Degradation of Collagen in the Bone–Resorbing Compartment Underlying the Osteoclast Involves Both Cysteine–Proteinases and Matrix Metalloproteinases", (1992), Journal of Cellular Physiology, 150, pp. 221–231.

Shi, et al., "Molecular cloning of human cathepsin O, a novel endoproteinase and homologue of rabbit OC2", (1995), FEBS Ltrs., 357, pp. 129–134.

Inaoka, et al., "Molecular Cloning of Human cDNA for Cathepsin K: Novel Cysteine Proteinase Predominantly Expressed in Bone", (1995), Biochemical and Biophysical Research Communications, 206 (1), pp. 89–96.

Elmore, et al., "A New Method for Determining the Absolute Molarity of Solutions of Trypsin and Chymotrypsin . . . ", (1968), Biochem J., 107, pp. 103–107.

Barker, et al., "The Reaction of an α–Aza–Amino Acid Derivative with Chymotrypsin and Its Use as a Ligand . . . ", (1974), Biochem J., 139, 555–563.

Gray, et al., "$N^\alpha$–Ethyloxycarbonyl–α–Azaornithine Phen . . . ", (1977), Tetrahedron, 33, p. 837–840.

Tezuka, et al., "Molecular Cloning of a Possible Cysteine Proteinase Predominantly Expressed in Osteoclasts", (1994), J. Biolog. Chem., 269 (2), pp. 1106–1109.

Gupton, et al., "Reaction of Azapeptides with Chymotrypsin–like Enzymes", (1984), J. Biol. Chem., 259:7, pp. 4279–4287.

U.S. patent application Ser. No. 09/463,000, Smith et al., filed Jan. 14, 2000.

McConnell, et al., "New Leupeptin Analogues: Synthesis and Inhibition Data", J. Med. Chem, 33, pp. 86–93.

Umezawa, "Structures and Activities of Protease Inhibitors of Microbial Origin", Meth. Enzymol., pp. 678–695.

Barrett, et al., "L–trans–Epoxysuccinyl–leucylamido(4–guanidino)butane (E–64) and its analogues . . . ", (1982), Biochem. J., 201, p. 189–198.

Han et al., Azatides: "Solution and Liquid Phase Syntheses of a New Peptidomimetic", (1986), J. Amer. Chem. Soc., 118:11, p. 2539–2544.

Grinde, "Selective Inhibition of Lysomal Protein Degradation By the Thiol Proteinase . . . " (1982), Biochem. J. Biophys. Acta., 701, pp. 328–333.

Baggio, et al., "From Poor Substrates to Good Inhibitors: Design of Inhibitors for Serine and Thiol Proteases", (1996), Biochem., 35:11, pp. 3351–3353.

Calabretta, et al., "Peptidyl and azapeptidyl methylketones as substrate analog inhibitors of papain and cathepsin B", (1995), Eur. J. Med. Chem., 30, pp. 931–941.

McConnell, et al., "Inhibition Studies of Some Serine and Thiol Proteinases by New Leupeptin Analogues", (1993), J. Med. Chem, 36, pp. 1084–1089.

Kawada, et al., "Polymer Compositions", (1971), Chemical Abstracts, vol. 83, DN 83: 180329; JP 50058142 (1975).

Castelhano, et al., "Synthesis, Chemistry and Absolute Configuration of Novel Transglutaminase Inhibitors Containing a 3–Halo–4,5–dihydroisoxazole", (1988), Bioorg. Chem., vol. 16, No. 3, pp. 335–340.

Greenlee, et al., "Azapeptides: A New Class of Angiotensin––Converting Enzyme Inhibitors", (1984), Biochem. & Biophys. Research Communications, 122:2, pp. 791–797.

Auger, et al., "Solid–State 13C NMR Study of a Transglutaminase–Inhibitor Adduct", (1993), Biochemistry, vol. 32, No. 15, pp. 3930–3934.

Database WPIDS on STN, Derwent Publications Ltd., (Columbus, Ohio), AN 85–029005, JP 59225172 A (Yamanouchi Pharm Co. Ltd), Abstract, (1984).

Thompson, et al., "Design of potent and selective human cathepsin K Inhibitors that span the active site", (1997), Proc. Natl. Acad. Sci. USA, 94, pp. 14249–14254.

Yamashita, et al., "Structure and Design of Potent and Selective Cathepsin K Inhibitors", (1997), J. Amer. Chem. Soc., 119, pp. 11351–11352.

U.S. patent application Ser. No. 09/653,815, Marquis, Jr. et al., filed Sep. 1, 2000.

Afridi, et al., "Heterocyclic Rearrangements. Part XIV. Attempts to Activate Ring–opening–Ring–closure Rearrangements with Carbon as the Central Atom", (1976), J.C.S. Perkin Trans I, vol. 3, pp. 315–320.

Kosary, et al., "Synthesis of pyridylthiazoles as antisecretory agents", (1989), Pharmazie, 44:3, pp. 191–193.

Sridevi, et al., "Some reactions and rearrangements of isoxazol–3–carbonyl azides and hydrazides", (1990), Indian J. of Chem., 29B:2, pp. 182–183.

Tanner, et al., "Total Synthesis of Balanol, Part 1. Enantioselective Synthesis of the Hexahydroazepine Ring via Chiral Epoxides and Axiridines", (1995), Tetrahedron, vol. 51, No. 21, pp. 6061–6070.

Winkler, "Molecular Molding Studies of "Flap Up" Mannosyl Cation Mimics", (1996), J. Med.Chem., 39, pp. 4332–4334.

PROTEASE INHIBITORS

This application is a 371 of PCT/US00/30684 filed Nov. 8, 2000 which claims the benefit Provisional Application filed Nov. 10, 1999.

FIELD OF THE INVENTION

This invention relates to a novel 4-amino-azepan-3-one protease inhibitor. This compound is particularly an inhibitor of cysteine and serine proteases, more particularly an inhibitor of cysteine proteases. The compound of this invention even more particularly inhibits cysteine proteases of the papain superfamily, and yet more particularly cysteine proteases of the cathepsin family. In the most preferred embodiment, this invention relates to a compound which inhibits cathepsin K. Such compound is particularly useful for treating diseases in which cysteine proteases are implicated, especially diseases of excessive bone or cartilage loss, e.g., osteoporosis, periodontitis, and arthritis.

BACKGROUND OF THE INVENTION

Cathepsin K is a member of the family of enzymes which are part of the papain superfamily of cysteine proteases. Cathepsins B, H, L, N and S have been described in the literature. Recently, cathepsin K polypeptide and the cDNA encoding such polypeptide were disclosed in U.S. Pat. No. 5,501,969 (called cathepsin O therein). Cathepsin K has been recently expressed, purified, and characterized. Bossard, M. J., et al., (1996) *J. Biol. Chem.* 271, 12517–12524; Drake, F. H., et al., (1996) *J. Biol. Chem.* 271, 12511–12516; Bromme, D., et al., (1996) *J. Biol. Chem.* 271, 2126–2132.

Cathepsin K has been variously denoted as cathepsin O, cathepsin X or cathepsin O2 in the literature. The designation cathepsin K is considered to be the more appropriate one (name assigned by Nomenclature Committee of the International Union of Biochemistry and Molecular Biology).

Cathepsins of the papain superfamily of cysteine proteases function in the normal physiological process of protein degradation in animals, including humans, e.g., in the degradation of connective tissue. However, elevated levels of these enzymes in the body can result in pathological conditions leading to disease. Thus, cathepsins have been implicated in various disease states, including but not limited to, infections by pneumocystis carinii, trypsanoma cruzi, trypsanoma brucei brucei, and Crithidia fusiculata; as well as in schistosomiasis malaria, tumor metastasis, metachromatic leukodystrophy, muscular dystrophy, amytrophy, and the like. See International Publication Number WO 94/04172, published on Mar. 3, 1994, and references cited therein. See also European Patent Application EP 0 603 873 A1, and references cited therein. Two bacterial cysteine proteases from *P. gingivallis*, called gingipains, have been implicated in the pathogenesis of gingivitis. Potempa, J., et al. (1994) Perspectives in *Drug Discovery and Design*, 2, 445–458.

Cathepsin K is believed to play a causative role in diseases of excessive bone or cartilage loss. Bone is composed of a protein matrix in which spindle- or plate-shaped crystals of hydroxyapatite are incorporated. Type I Collagen represents the major structural protein of bone comprising approximately 90% of the structural protein. The remaining 10% of matrix is composed of a number of non-collagenous proteins, including osteocalcin, proteoglycans, osteopontin, osteonectin, thrombospondin, fibronectin, and bone sialoprotein. Skeletal bone undergoes remodeling at discrete foci throughout life. These foci, or remodeling units, undergo a cycle consisting of a bone resorption phase followed by a phase of bone replacement.

Bone resorption is carried out by osteoclasts, which are multinuclear cells of hematopoietic lineage. The osteoclasts adhere to the bone surface and form a tight sealing zone, followed by extensive membrane ruffling on their apical (i.e., resorbing) surface. This creates an enclosed extracellular compartment on the bone surface that is acidified by proton pumps in the ruffled membrane, and into which the osteoclast secretes proteolytic enzymes. The low pH of the compartment dissolves hydroxyapatite crystals at the bone surface, while the proteolytic enzymes digest the protein matrix. In this way, a resorption lacuna, or pit, is formed. At the end of this phase of the cycle, osteoblasts lay down a new protein matrix that is subsequently mineralized. In several disease states, such as osteoporosis and Paget's disease, the normal balance between bone resorption and formation is disrupted, and there is a net loss of bone at each cycle. Ultimately, this leads to weakening of the bone and may result in increased fracture risk with minimal trauma.

The abundant selective expression of cathepsin K in osteoclasts strongly suggests that this enzyme is essential for bone resorption. Thus, selective inhibition of cathepsin K may provide an effective treatment for diseases of excessive bone loss, including, but not limited to, osteoporosis, gingival diseases such as gingivitis and periodontitis, Paget's disease, hypercalcemia of malignancy, and metabolic bone disease. Cathepsin K levels have also been demonstrated to be elevated in chondroclasts of osteoarthritic synovium. Thus, selective inhibition of cathepsin K may also be useful for treating diseases of excessive cartilage or matrix degradation, including, but not limited to, osteoarthritis and rheumatoid arthritis. Metastatic neoplastic cells also typically express high levels of proteolytic enzymes that degrade the surrounding matrix. Thus, selective inhibition of cathepsin K may also be useful for treating certain neoplastic diseases.

It now has been discovered that a certain novel compound is a protease inhibitor, most particularly an inhibitor of cathepsin K, and that this compound is useful for treating diseases characterized by bone loss, such as osteoporosis and gingival diseases, such as gingivitis and periodontitis, or by excessive cartilage or matrix degradation, such as osteoarthritis and rheumatoid arthritis.

SUMMARY OF THE INVENTION

An object of the present invention is to provide a 4-amino-azepan-3-one protease inhibitor, particularly an inhibitor of cysteine and serine proteases. More particularly, the present invention relates to such a compound which inhibits cysteine proteases, and yet more particularly cysteine proteases of the papain superfamily. Preferably, this invention relates to such a compound which inhibits cysteine proteases of the cathepsin family and most preferably, a compound which inhibits cathepsin K. The compound of the present invention is useful for treating diseases which may be therapeutically modified by altering the activity of such proteases.

Accordingly, in the first aspect, this invention provides a compound, quinoline-2-carboxylic acid {(S)-3-methyl-1-[3-oxo-1-(1-oxy-pyridine-2-sulfonyl)-azepan-4-ylcarbamoyl]-butyl}amide, according to Formula I:

(I)

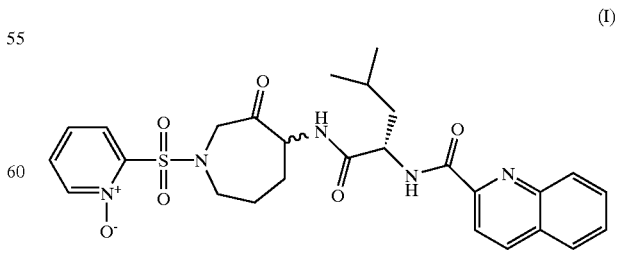

In another aspect, this invention provides a pharmaceutical composition comprising a compound according to Formula I and a pharmaceutically acceptable carrier.

In yet another aspect, this invention provides a method of treating diseases in which the disease pathology may be therapeutically modified by inhibiting proteases, such as cysteine and serine proteases. In particular, the method includes treating diseases by inhibiting cysteine proteases, and particularly cysteine proteases of the papain superfamily. More particularly, the inhibition of cysteine proteases of the cathepsin family, such as cathepsin K is described.

In another aspect, the compound of this invention is especially useful for treating diseases characterized by bone loss, such as osteoporosis, and gingival diseases, such as gingivitis and periodontitis, or by excessive cartilage or matrix degradation, such as osteoarthritis and rheumatoid arthritis.

DETAILED DESCRIPTION OF THE INVENTION

The present invention provides a compound, quinoline-2-carboxylic acid {-(S)3-methyl-1-[3-oxo-1-(1-oxy-pyridine-2-sulfonyl)-azepan-4-ylcarbamoyl]-butyl}amide, of Formula (I):

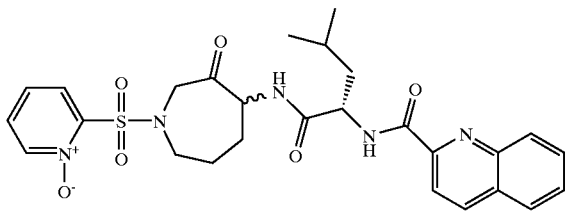

(I)

or a pharmaceutically acceptable salt, hydrate or solvate thereof.

The present invention includes all hydrates, solvates, complexes, polymorphs and prodrugs of the compound of Formula (I). Prodrugs are any covalently bonded compounds which release the active parent drug according to Formula (I) in vivo. Prodrugs of the compound of the present invention include ketone derivatives, specifically ketals or hemiketals.

All forms of isomers resulting from the presence of a chiral center in the inventive compound, including enantiomers and diastereomers, are intended to be covered herein. The inventive compound may be used as a racemic mixture, an enantiomerically enriched mixture, or the racemic mixture may be separated using well-known techniques and an individual enantiomer may be used alone.

In the event that the present compound may exist in tautomeric forms, such as keto-enol tautomers, each tautomeric form is contemplated as being included within this invention whether existing in equilibrium or predominantly in one form.

Compared to the corresponding 5 and 6 membered ring compounds, the 7 membered ring compound of the present invention is configurationally more stable at the carbon center alpha to the ketone.

Definitions

Abbreviations and symbols commonly used in the peptide and chemical arts are used herein to describe the compounds of the present invention. In general, the amino acid abbreviations follow the IUPAC-IUB Joint Commission on Biochemical Nomenclature as described in *Eur. J. Biochem.*, 158, 9 (1984). In particular, throughout this application, m-CPBA means meta-chloroperoxybenzoic acid; Boc means tert-butoxycarbonyl; EDC means 1-(3-dimethylaminopropyl)-3-ethylcarbodiimide hydrochloride; DMSO means methyl sulfoxide; and TEA means triethylamine.

Method of Preparation

The compound of the Formula (I) is generally prepared according to Scheme 1. The individual diastereomers of quinoline-2-carboxylic acid {(S)-3-methyl-1-[3-oxo-1-(1-oxy-pyridine-2-sulfonyl)-azepan-4-ylcarbamoyl]-butyl}amide 10 and 11 may be prepared as outlined in Scheme 1. Alkylation of allyl-carbamic acid benzyl ester (1) with 5-bromo-1-pentene in the presence of a base such as sodium hydride provides the diene 2. Treatment of diene 2 with bis(tricyclohexylphosphine)benzylidine ruthenium (IV) dichloride provides the 2,3,4,7-tetrahydro-azepine-1-carboxylic acid benzyl ester 3. Epoxidation of azepine 3 may be effected with standard oxidizing agents common to the art such as m-CPBA to provide epoxide 4. Nucleophilic epoxide ring opening of 4 may be effected with a reagent such as sodium azide to provide the azido alcohol (not shown). The intermediate azido alcohol may be reduced to the amino alcohol 5 under conditions common to the art such as 1,3-propanedithiol and triethylamine Scheme 1

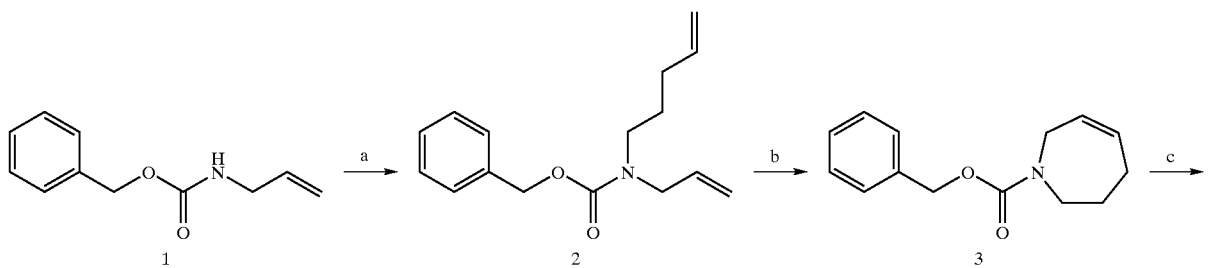

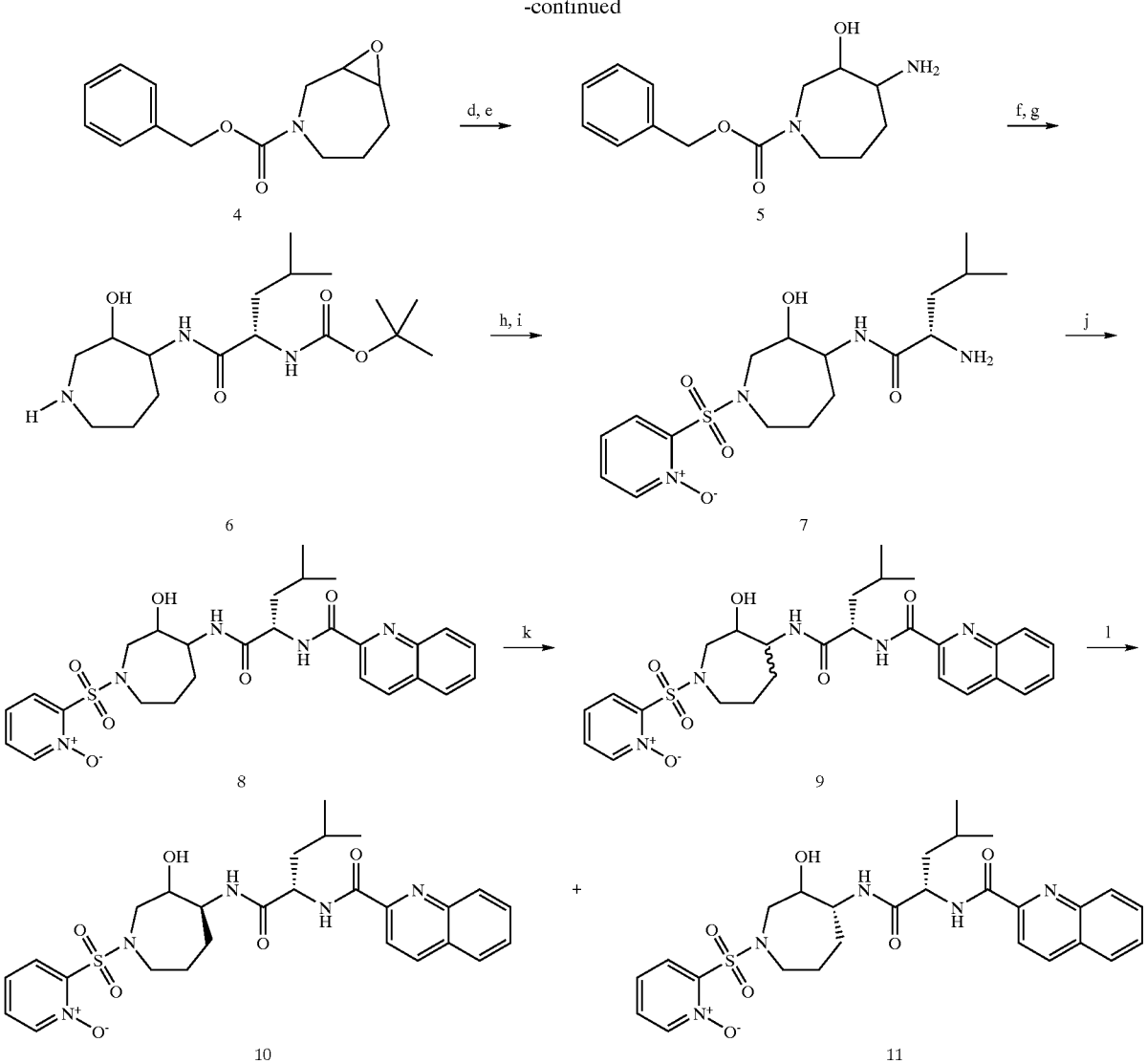

Reagents and Conditions: a.) NaH, 5-bromo-1-pentene, DMF; b.) bis(tricyclohexylphosphine)benzylidine ruthenium (IV) dichloride, $CH_2Cl_2$; c.) m-CPBA, $CH_2Cl_2$; d.) $NaN_3$, $CH_3OH$, $H_2O$, $NH_4Cl$; e.) 1,3-propanedithiol, TEA, methanol; f.) N-Boc-leucine, EDC, $CH_2Cl_2$; g.) 10% Pd/C, $H_2$; h.) 2-pyridinesulphonyl chloride-N-oxide, saturated. $NaHCO_3$, $CH_2Cl_2$; i.) 4N HCl/dioxane, methanol; j.) quinoline-2-carboxylic acid, EDC, $CH_2Cl_2$; k.) pyridine sulfur trioxide complex, DMSO, TEA; l.) HPLC separation. in methanol or with triphenylphosphine in tetrahydrofuran and water. Acylation of 5 may be effected with an acid such as N-Boc-leucine in the presence of a coupling agent such as EDC. Removal of the benzyloxycarbonyl protecting group with hydrogen gas in the presence of 10% Pd/C provides the amine 6. Treatment of the amine 6 with 2-pyridinesulphonylchloride-N-oxide in the presence of saturated sodium bicarbonate and dichloromethane followed by removal of the tert-butoxycarbonyl protecting group under acidic conditions provides 7. Coupling of 7 with quinoline-2-carboxylic acid may be effected with a coupling agent such as EDC to provide intermediate alcohol 8. Alcohol 8 may be oxidized with an oxidant such as sulfur trioxide pyridine complex in DMSO and triethylamine to provide the ketone 9 as a mixture of diastereomers. The diastereomers 9 may be separated by HPLC to provide compounds 10 and 11.

The starting materials used herein are commercially available or are prepared by routine methods well known to those of ordinary skill in the art and can be found in standard reference books, such as the COMPENDIUM OF ORGANIC SYNTHETIC METHODS, Vol. I-VI (published by Wiley-Interscience).

Coupling methods to form amide bonds herein are generally well-known in the art. The methods of peptide synthesis generally set forth by Bodansky et al., THE PRACTICE OF PEPTIDE SYNTHESIS, Springer-Verlag, Berlin, 1984; E. Gross and J. Meienhofer, THE PEPTIDES, Vol. 1, 1–284 (1979); and J. M. Stewart and J. D. Young, SOLID PHASE PEPTIDE SYNTHESIS, 2d Ed., Pierce Chemical Co., Rockford, Ill., 1984, are generally illustrative of the technique and are incorporated herein by reference.

Synthetic methods useful in preparing the compound of this invention frequently employ protective groups to mask a reactive functionality or minimize unwanted side reactions. Such protective groups are described generally in Green, T.W, PROTECTIVE GROUPS IN ORGANIC SYNTHESIS, John Wiley & Sons, New York (1981). The term "amino protecting groups" generally refers to the Boc, acetyl, benzoyl, Fmoc and Cbz groups and derivatives thereof as known to the art. Methods for protection and deprotection, and replacement of an amino protecting group with another moiety are well known.

Acid addition salts of the compound of Formula (I) are prepared in a standard manner in a suitable solvent from the parent compound and an excess of an acid, such as hydrochloric, hydrobromic, hydrofluoric, sulfuric, phosphoric, acetic, trifluoroacetic, maleic, succinic or methanesulfonic acid.

Novel Intermediate

The present invention also provides a novel intermediate, quinoline-2-carboxylic acid {(S)-3-methyl-1-[3-hydroxy-1-(1-oxy-pyridine-2-sulfonyl)-azepan-4-ylcarbamoyl]-butyl}amide (8-Scheme-1), of Formula (II), useful in the synthesis of the compound of Formula (I) according to Scheme 1.

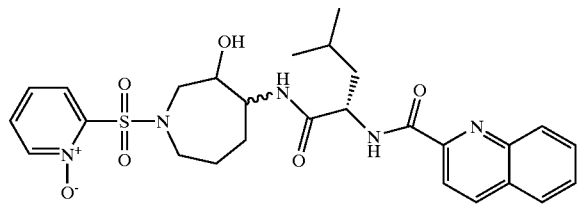

(II)

Process for Synthesis of Inventive Compounds

Referring to Scheme 1 herein above, the present invention provides a process for the synthesis of compounds of Formula (I) comprising the step of oxidizing the appropriate compound of Formula (II) with an oxidant to provide the compound of Formula (I) as a mixture of diastereomers. Preferably the oxidant is sulfur trioxide pyridine complex in DMSO and triethylamine.

The process further comprises the step of separating the diasteromers of Formula (I) by separating means, preferably by high pressure liquid chromatography (HPLC).

Utility of the Present Invention

This invention also provides a pharmaceutical composition which comprises a compound according to Formula (I) and a pharmaceutically acceptable carrier, excipient or diluent. Accordingly, the compound of Formula (I) may be used in the manufacture of a medicament. Pharmaceutical compositions of the compound of Formula (I) prepared as hereinbefore described may be formulated as solutions or lyophilized powders for parenteral administration. Powders may be reconstituted by addition of a suitable diluent or other pharmaceutically acceptable carrier prior to use. The liquid formulation may be a buffered, isotonic, aqueous solution. Examples of suitable diluents are normal isotonic saline solution, standard 5% dextrose in water, or buffered sodium or ammonium acetate solution. Such formulation is especially suitable for parenteral administration, but may also be used for oral administration or contained in a metered dose inhaler or nebulizer for insufflation. It may be desirable to add excipients such as polyvinylpyrrolidone, gelatin, hydroxy cellulose, acacia, polyethylene glycol, mannitol, sodium chloride, or sodium citrate.

Alternately, this compound may be encapsulated, tableted, or prepared in an emulsion or syrup for oral administration. Pharmaceutically acceptable solid or liquid carriers may be added to enhance or stabilize the composition, or to facilitate preparation of the composition. Solid carriers include starch, lactose, calcium sulfate dihydrate, terra alba, magnesium stearate or stearic acid, talc, pectin, acacia, agar or gelatin. Liquid carriers include syrup, peanut oil, olive oil, saline and water. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulating, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly or filled into a soft gelatin capsule.

For rectal administration, the compound of this invention may also be combined with excipients such as cocoa butter, glycerin, gelatin or polyethylene glycols and molded into a suppository.

The compound of Formula (I) is useful as a protease inhibitor, particularly as an inhibitor of cysteine and serine proteases, more particularly as an inhibitor of cysteine proteases, even more particularly as an inhibitor of cysteine proteases of the papain superfamily, yet more particularly as an inhibitor of cysteine proteases of the cathepsin family, most particularly as an inhibitor of cathepsin K. The present invention also provides useful compositions and formulations of said compound, including pharmaceutical compositions and formulations of said compound.

The present compound is useful for treating diseases in which cysteine proteases are implicated, including infections by pneumocystis carinii, trypsanoma cruzi, trypsanoma brucei, and Crithidia fusiculata; as well as in schistosomiasis, malaria, tumor metastasis, metachromatic leukodystrophy, muscular dystrophy, amytrophy; and especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis, Paget's disease; hypercalcemia of malignancy, and metabolic bone disease.

Metastatic neoplastic cells also typically express high levels of proteolytic enzymes that degrade the surrounding matrix, and certain tumors and metastatic neoplasias may be effectively treated with the compound of this invention.

The present invention also provides methods of treatment of diseases caused by pathological levels of proteases, particularly cysteine and serine proteases, more particularly cysteine proteases, even more particularly cysteine proteases of the papain superfamily, yet more particularly cysteine proteases of the cathepsin family, which methods comprise administering to an animal, particularly a mammal, most particularly a human in need thereof the compound of the present invention. The present invention especially provides methods of treatment of diseases caused by pathological levels of cathepsin K, which methods comprise administering to an animal, particularly a mammal, most particularly a human in need thereof, an inhibitor of cathepsin K, including the compound of the present invention. The present invention particularly provides methods for treating diseases in which cysteine proteases are implicated, including infections by pneumocystis carinii, trypsanoma cruzi, trypsanoma brucei, and Crithidia fusiculata; as well as in schistosomiasis, malaria, tumor metastasis, metachromatic leukodystrophy, muscular dystrophy, amytrophy, and especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis, Paget's disease, hypercalcemia of malignancy, and metabolic bone disease.

This invention further provides a method for treating osteoporosis or inhibiting bone loss which comprises internal administration to a patient of an effective amount of the compound of Formula (I), alone or in combination with other inhibitors of bone resorption, such as bisphosphonates (i.e., allendronate), hormone replacement therapy, anti-estrogens, or calcitonin. In addition, treatment with the compound of this invention and an anabolic agent, such as bone morphogenic protein, iproflavone, may be used to prevent bone loss or to increase bone mass.

In accordance with this invention, an effective amount of the compound of Formula (I) is administered to inhibit the protease implicated in a particular condition or disease. Of course, this dosage amount will further be modified according to the type of administration of the compound. For example, for acute therapy, parenteral administration of the compound of Formula (I) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit cathepsin K. The compound is administered one to four times daily at a level to achieve a total daily dose of about 0.4 to about 400 mg/kg/day. The precise amount of the inventive compound which is therapeutically effective, and the route by which such compound is best administered, is readily determined by one of ordinary skill in the art by comparing the blood level of the agent to the concentration required to have a therapeutic effect.

Prodrugs of the compound of the present invention may be prepared by any suitable method. Where the prodrug moiety is a ketone functionality, specifically ketals and/or hemiacetals, the conversion may be effected in accordance with conventional methods.

The compound of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention.

Biological Assays

The compound of this invention may be tested in one of several biological assays to determine the concentration of the compound which is required to have a given pharmacological effect.

Determination of Cathepsin K Proteolytic Catalytic Activity

All assays for cathepsin K were carried out with human recombinant enzyme. Standard assay conditions for the determination of kinetic constants used a fluorogenic peptide substrate, typically Cbz-Phe-Arg-AMC, and were determined in 100 mM Na acetate at pH 5.5 containing 20 mM cysteine and 5 mM EDTA. Stock substrate solutions were prepared at concentrations of 10 or 20 mM in DMSO with 20 $\mu$M final substrate concentration in the assays. All assays contained 10% DMSO. Independent experiments found that this level of DMSO had no effect on enzyme activity or kinetic constants. All assays were conducted at ambient temperature. Product fluorescence (excitation at 360 nM; emission at 460 nM) was monitored with a Perceptive Biosystems Cytofluor II fluorescent plate reader. Product progress curves were generated over 20 to 30 minutes following formation of AMC product.

Inhibition Studies

Potential inhibitors were evaluated using the progress curve method. Assays were carried out in the presence of variable concentrations of test compound. Reactions were initiated by addition of enzyme to buffered solutions of inhibitor and substrate. Data analysis was conducted according to one of two procedures depending on the appearance of the progress curves in the presence of inhibitors. For those compounds whose progress curves were linear, apparent inhibition constants ($K_{i,app}$) were calculated according to equation 1 (Brandt et al., *Biochemitsry*, 1989, 28, 140):

$$v = V_m A / [K_a(1+I/K_{i,app}) + A] \quad (1)$$

where v is the velocity of the reaction with maximal velocity $V_m$, A is the concentration of substrate with Michaelis constant of $K_a$, and I is the concentration of inhibitor.

For those compounds whose progress curves showed downward curvature characteristic of time-dependent inhibition, the data from individual sets was analyzed to give $k_{obs}$ according to equation 2:

$$[AMC] = v_{ss}t + (v_0 - v_{ss})[1 - \exp(-k_{obs}t)]/k_{obs} \quad (2)$$

where [AMC] is the concentration of product formed over time t, $v_0$ is the initial reaction velocity, and $v_{ss}$ is the final steady state rate. Values for $k_{obs}$ were then analyzed as a linear function of inhibitor concentration to generate an apparent second order rate constant ($k_{obs}$/inhibitor concentration or $k_{obs}/[I]$) describing the time-dependent inhibition. A complete discussion of this kinetic treatment has been fully described (Morrison et al., *Adv. Enzymol. Relat. Areas Mol. Biol.*, 1988, 61, 201).

One skilled in the art would consider any compound with a $K_i$ of less than 50 micromolar to be a potential lead compound. Preferably, the compounds used in the method of the present invention have a $K_i$ value of less than 1 micromolar. Most preferably, said compounds have a $K_i$ value of less than 100 nanomolar.

Human Osteoclast Resorption Assay

Aliquots of osteoclastoma-derived cell suspensions were removed from liquid nitrogen storage, warmed rapidly at 37° C. and washed ×1 in RPMI-1640 medium by centrifugation (1000 rpm, 5 min at 4° C.). The medium was aspirated and replaced with murine anti-HLA-DR antibody, diluted 1:3 in RPMI-1640 medium, and incubated for 30 minutes on ice. The cell suspension was mixed frequently.

The cells were washed ×2 with cold RPMI-1640 by centrifugation (1000 rpm, 5 min at 4° C.) and then transferred to a sterile 15 mL centrifuge tube. The number of mononuclear cells were enumerated in an improved Neubauer counting chamber.

Sufficient magnetic beads (5/mononuclear cell), coated with goat anti-mouse IgG, were removed from their stock bottle and placed into 5 mL of fresh medium (this washes away the toxic azide preservative). The medium was removed by immobilizing the beads on a magnet and is replaced with fresh medium.

The beads were mixed with the cells and the suspension was incubated for 30 minutes on ice. The suspension was mixed frequently. The bead-coated cells were immobilized on a magnet and the remaining cells (osteoclast-rich fraction) were decanted into a sterile 50 mL centrifuge tube. Fresh medium was added to the bead-coated cells to dislodge any trapped osteoclasts. This wash process was repeated ×10. The bead-coated cells were discarded.

The osteoclasts were enumerated in a counting chamber, using a large-bore disposable plastic pasteur pipette to charge the chamber with the sample. The cells were pelleted by centrifugation and the density of osteoclasts adjusted to $1.5 \times 10^4$/mL in EMEM medium, supplemented with 10% fetal calf serum and 1.7 g/litre of sodium bicarbonate. 3 mL aliquots of the cell suspension ( per treatment) were decanted into 15 mL centrifuge tubes. These cells were pelleted by centrifugation. To each tube 3 mL of the appropriate treatment was added (diluted to 50 $\mu$M in the EMEM medium). Also included were appropriate vehicle controls, a positive control (87MEM1 diluted to 100 ug/mL) and an isotype control (IgG2a diluted to 100 ug/mL). The tubes were incubated at 37° C. for 30 minutes.

0.5 mL aliquots of the cells were seeded onto sterile dentine slices in a 48-well plate and incubated at 37° C. for 2 hours. Each treatment was screened in quadruplicate. The slices were washed in six changes of warm PBS (10 mL/well in a 6-well plate) and then placed into fresh treatment or control and incubated at 37° C. for 48 hours. The slices were then washed in phosphate buffered saline and fixed in 2% glutaraldehyde (in 0.2 M sodium cacodylate) for 5 minutes, following which they were washed in water and incubated in buffer for 5 minutes at 37° C. The slices were then washed in cold water and incubated in cold acetate buffer/fast red garnet for 5 minutes at 4° C. Excess buffer was aspirated, and the slices were air dried following a wash in water.

The TRAP positive osteoclasts were enumerated by bright-field microscopy and were then removed from the surface of the dentine by sonication. Pit volumes were determined using the Nikon/Lasertec ILM21W confocal microscope.

EXAMPLES

In the following synthetic examples, unless otherwise indicated, all of the starting materials were obtained from commercial sources. Without further elaboration, it is believed that one skilled in the art can, using the preceding description, utilize the present invention to its fullest extent. These Examples are given to illustrate the invention, not to limit its scope. Reference is made to the claims for what is reserved to the inventors hereunder.

Example 1

Preparation of Quinoline-2-carboxylic acid {(S)-3-methyl-1-[3-oxo-1-(1-oxy-pyridine-2-sulfonyl-azepan-4-ylcarbamoyl]-butyl}amide a.) Allyl-pent-4-enyl-carbamic Acid Benzyl Ester To a suspension of NaH (1.83 g, 76.33 mmol of 90% NaH) in DMF was added allyl-carbamic acid benzyl ester (7.3 g, 38.2 mmol) in a dropwise fashion. The mixture was stirred at room temperature for approximately 10 minutes whereupon 5-bromo-1-pentene (6.78 mL, 57.24 mmol) was added in a dropwise fashion. The reaction was heated to 40° C. for approximately 4 hours whereupon the reaction was partitioned between dichloromethane and water. The organic layer was washed with water (2×'s), brine, dried (MgSO$_4$), filtered and concentrated. Column chromatography of the residue (10% ethyl acetate:hexanes) provided 10.3 grams of the title compound as an oil: MS(EI) 260 (M+H$^+$).

b.) 2,3,4,7-Tetrahydro-azepine-1-carboxylic Acid Benzyl Ester

To a solution of compound of Example 1a (50 g) in dichloromethane was added bis(tricyclohexylphosphine) benzylidine ruthenium (IV) dichloride (5.0 g). The reaction was heated to reflux until complete as determined by TLC analysis. The reaction was concentrated in vacuo. Column chromatography of the residue (50% dichloromethane:hexanes) gave 35 g of the title compound: MS(EI) 232 (M+H$^+$).

c.) 8-Oxa-3-aza-bicyclo[5.1.0]Octane-3-carboxylic Acid Benzyl Ester

To a solution of the compound of Example 1b (35 g, 1.5 mol) in CH$_2$Cl$_2$ was added m-CPBA (78 g, 0.45 mol). The mixture was stirred overnight at room temperature whereupon it was filtered to remove the solids. The filtrate was washed with water and saturated NaHCO$_3$ (several times). The organic layer was dried (MgSO$_4$), filtered and concentrated to give 35 g of the title compound which was of sufficient purity to carry on to the next step: MS(EI) 248 (M+H$^+$), 270 (M+Na$^+$).

d. 4-Azido-3-hydroxy-azepane-1-carboxylic Acid Benzyl Ester

To a solution of the epoxide from Example 1c (2.0 g, 8.1 mmol) in methanol:water (8:1 solution) was added NH$_4$Cl (1.29 g, 24.3 mmol) and sodium azide (1.58 g, 24.30 mmol). The reaction was heated to 65–75° C. until complete consumption of the starting epoxide was observed by TLC analysis. The majority of the solvent was removed in vacuo and the remaining solution was partitioned between ethyl acetate and pH 4 buffer. The organic layer was washed with sat. NaHCO$_3$, water, brine dried (MgSO$_4$), filtered and concentrated. Column chromatography (20% ethyl acetate:hexanes) of the residue provided 1.3 g of the title compound: MS(EI) 291 (M+H$^+$) plus 0.14 g of trans4-hydroxy-3-azido-hexahydro-1H-azepine e.) 4-Amino-3-hydroxy-azepane-1-carboxylic Acid Benzyl Ester To a solution of the azido alcohol of Example 1d (1.1 g, 3.79 mmol) in methanol was added triethyamine (1.5 mL, 11.37 mmol) and 1,3-propanedithiol (1.1 mL, 11.37 mmoL). The reaction was stirred until complete consumption of the starting material was observed by TLC analysis whereupon the reaction was concentrated in vacuo. Column chromatography of the residue (20% methanol:dichloromethane) provided 0.72 g of the title compound: MS(EI) 265 (M+H$^+$).

f.) 4-((S)-2-tert-Butoxycarbonylamino-4-methyl-pentanoylamino)-3-hydroxy-azepan-1-carboxylic Acid Benzyl Ester To a solution of the amino alcohol of Example 1e (720 mg, 2.72 mmol) in CH$_2$Cl$_2$ was added EDC (521 mg), HOBt (368 mg) and N-Boc-leucine (630 mg). The reaction was maintained at room temperature until complete consumption of the starting material was observed by TLC analysis. The reaction was diluted with ethyl acetate and washed with 1N HCl, sat. K$_2$CO$_3$, water, brine, dried (MgSO$_4$), filtered and concentrated. Column chromatography of the residue (3% methanol:dichloromethane) gave 1.0 g of the title compound: MS(EI) 478 (M+H$^+$).

g.) [(S)-1-(3-Hydroxy-azepan-4-ylcarbamoyl)-3-methyl-butyl]-carbamic Acid Tert Butyl Ester To a solution of the compound of Example 1f (1.0 g) and 10% Pd/C (catalytic) in ethyl acetate:methanol (2:1 solution) was attached a balloon of hydrogen. The reaction was stirred until complete consumption of the starting material was observed by TLC analysis. The reaction was filtered to remove the catalyst and the filtrate was concentrated to provide 0.82 g of the title compound: MS(EI) 344 (M+H$^+$).

h.) {(S)-1-[3-Hydroxy-1-(1-oxy-pyridine-2-sulfonyl)-azepan4-ylcarbamoyl]-3-methyl-butyl}-carbamic Acid Tert-butyl Ester Generation of 2-pyridinesulfonyl chloride-N-oxide: To a 0° C. solution of 2-mercaptopyridine-N-oxide (2.23 g, 17.55 mmol) in 9M HCl (33 mL) was bubbled chlorine gas for approximately 90 minutes. The dissolved chlorine was removed under vacuum at 0° C.

To a solution of [(S)-1-(3-hydroxy-azepan-4-ylcarbamoyl)-3-methyl-butyl]-carbamic acid tert butyl ester of Example 1g (2.5 g, 7.28 mmol) in CH$_2$Cl$_2$ (100 mL) and sat. NaHCO$_3$ (400 mL) was added the solution of 2-pyridinesulfonyl chloride-N-oxide (27 mL, 102 mg/mL) dropwise in portions. As the addition proceeds additional sat. NaHCO$_3$ is added in order to maintain the pH at approximately 8–9. Upon complete addition of the sulfonylchloride the reaction is stirred for an additional hour whereupon the organic layer was removed and washed with brine. The organic layer was evaporated and the residue chromatographed (5% methanol:dichloromethane) to provide 2.5 g of the title compound: MS (EI) 500 (M+H$^+$).

i.) (S)-2-Amino4-methyl-pentanoic acid-[3-hydroxy- 1-(1-oxy-pyridine-2-sulfonyl)-azepan-4-yl]-amide To a solution of {(S)-1-[3-hydroxy-1-(1-oxy-pyridine-2-sulfonyl)-azepan-4-ylcarbamoyl]-3-methyl-butyl}-carbamic acid tert-butyl ester of Example 1h (2.0 g) in methanol (20 mL) was added 4 M HCl in dioxane (20 mL). The reaction was stirred at room temperature for 1.5 hours whereupon it was concentrated to provide 1.8 g of the title compound: MS (EI) 400 (M+H$^+$).

j.) Quinoline-2-carboxylic acid {(S)-3-methyl-1-[3-hydroxy-1-(1-oxy-pyridine-2-sulfonyl)-azepan-4-ylcarbamoyl]-butyl}amide To a solution of the compound of Example 1i (320 mg, 0.73 mmol) in CH$_2$Cl$_2$ was added triethylamine (0.15 mL, 1.09 mmol), EDC (140 mg, 0.73 mmol), HOBt (99 mg, 0.73 mmol) and quinoline-2-carboxylic acid (126 mg, 0.73 mmol). The reaction was stirred until complete by TLC analysis. Workup and column chromatography of the residue gave 260 mg of the title compound: MS(EI) 555 (M$^+$).

k.) Quinoline-2-carboxylic acid {(S)-3-methyl-1-[3-oxo-1-(1-oxy-pyridine-2-sulfonyl)-azepan-4-ylcarbamoyl]-butyl}amide To a solution of the alcohol of Example 1j (0.26 g, 0.47 mmol) in DMSO was added TEA (0.39 mL, 2.8 mmol) and pyridine sulfur trioxide complex (222 mg, 1.4 mmol). The reaction was stirred at room temperature for ca. 2 hours whereupon it was partitioned between ethyl acetate and water. The organic layer was washed with brine, dried, filtered and concentrated. Column chromatography of the residue (10% CH$_3$OH:CH$_2$Cl$_2$) provided 240 mg of the title compound as a mixture of diastereomers: : $^1$H NMR (CDCl$_3$): δ1.0 (m, 6H), 1.5–2.1 (m, 5H), 2.2 (m, 2H), 2.7 (m, 1H), 3.8 (q, 1H), 4.0 (m, 1H), 4.5 (t, 1H), 4.7 (m, 1H), 5.0 (m, 1H), 7.4–8.6 (m, 10H); MS(EI): 553 (M$^+$,100%).

The diastereomeric mixture was separated by HPLC to provide the faster eluting diastereoemer; MS(EI): 554 (M+H$^+$,100%) and the slower eluting diastereomer; MS(EI): 554 (M+H$^+$,100%).

K$_i$=0.41 nM.

Pit Assay=300 nM.

The above specification and Example fully disclose how to make and use the compound of the present invention. However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

What is claimed is:

1. A compound according to Formula (I):

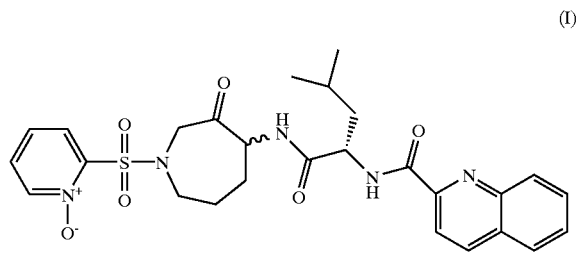

known as quinoline-2-carboxylic acid {(S)-3-methyl-1-[3-oxo-1-(1-oxy-pyridine-2-sulfony)-azepan-4-ylcarbamoyl]-butyl}amide, or a pharmaceutically acceptable salt, hydrate or solvate thereof.

2. A pharmaceutical composition comprising a compound according to claim 1 and a pharmaceutically acceptable carrier, excipient or diluent.

3. A method of inhibiting a protease selected from the group consisting of a cysteine protease and a serine protease, comprising administering to a patient in need thereof an effective amount of a compound according to claim 1.

4. A method according to claim 3 wherein said protease is a cysteine protease.

5. A method according to claim 4 wherein said cysteine protease is cathepsin K.

6. A method of treating a disease characterized by bone loss comprising inhibiting said bone loss by administering to a patient in need thereof an effective amount of a compound according to claim 1.

7. A method according to claim 6 wherein said disease is osteoporosis.

8. A method according to claim 6 wherein said disease is periodontitis.

9. A method according to claim 6 wherein said disease is gingivitis.

10. A method of treating a disease characterized by excessive cartilage or matrix degradation comprising inhibiting said excessive cartilage or matrix degradation by administering to a patient in need thereof an effective amount of a compound according to claim 1.

11. A method according to claim 10 wherein said disease is osteoarthritis.

12. A method according to claim 10 wherein said disease is rheumatoid arthritis.

13. A compound according to Formula (II):

(II)

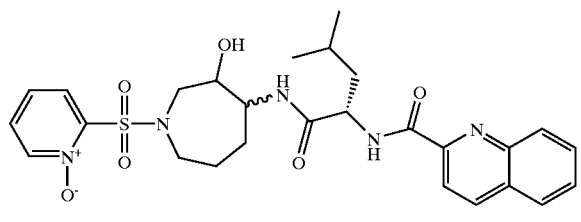

known as quinoline-2-carboxylic acid {(S)-3-methyl-1-[3-hydroxy-1-(1-oxy-pyridine-2-sulfonyl)-azepan-4-ylcarbamoyl]-butyl}amide,
or a pharmaceutically acceptable salt, hydrate or solvate thereof.

14. A process for the synthesis of the compound of Formula (I):

(I)

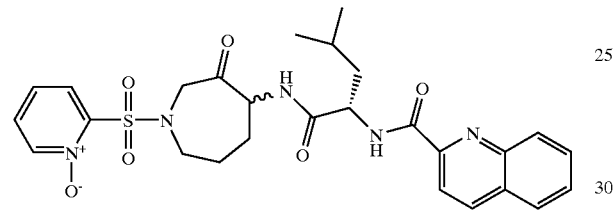

comprising the step of oxidizing the compound of Formula (II):

(II)

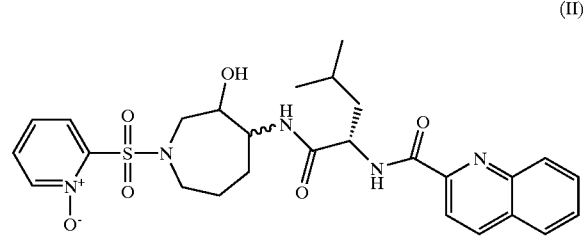

with an oxidant to provide the compound of Formula (I) as a mixture of diastereomers.

15. The process of claim 14 therein the oxidant is sulfur trioxide pyridine complex in DMSO and triethylamine.

16. The process of claim 14 further comprising the step of separating the diasteromers by separating means.

17. The process of claim 16 wherein said separating means is high pressure liquid chromatography (HPLC).

* * * * *